United States Patent [19]

Ogilvie

[11] 4,347,360
[45] Aug. 31, 1982

[54] RING OPEN NUCLEOSIDE ANALOGUES

[75] Inventor: Kelvin K. Ogilvie, Candiac, Canada

[73] Assignee: ens BIO LOGICALS Inc., Toronto, Canada

[21] Appl. No.: 187,631

[22] Filed: Sep. 16, 1980

[51] Int. Cl.³ ............... C07D 473/18; C07D 473/34
[52] U.S. Cl. ............................ 544/276; 544/298; 544/309; 544/313; 544/277; 536/23; 536/24; 536/26; 424/251; 424/253
[58] Field of Search .......................... 544/277, 276

[56] References Cited

U.S. PATENT DOCUMENTS 4,158,056  6/1979  Nagarajan ............... 424/257
4,199,574  4/1980  Schaeffer ................ 544/277

OTHER PUBLICATIONS

Bryant et al., J. Org. Chem., 44, (21), 3733, 1979.
Gillen, M. F., Dissertation Abst. International, vol. 41, No, 8, Feb. 1981.
Gillen, M. F., "Synthesis and Properties of Novel Nucleoside and Nucleotide Analogues", pp. 1-83, Apr. 1980.
Ogilive, et al., Tetrahedron Letters, vol. 21, pp. 327-330, 1980.

Primary Examiner—Donald G. Daus
Assistant Examiner—Sharon A. Gibson
Attorney, Agent, or Firm—Fleit & Jacobson

[57] ABSTRACT

Nucleoside analogues having a ring-open structure, of general formula:

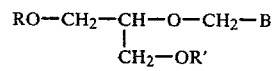

where R and R' may be hydrogen, silyl groups, substituted alkyl groups and the like, and B is a base such as adenine, have been shown to exhibit anti-viral and other biological activities at non-toxic levels. Also provided are phosphate-linked dinucleotide compounds of similar structures.

6 Claims, No Drawings

RING OPEN NUCLEOSIDE ANALOGUES

FIELD OF THE INVENTION

This invention relates to novel compositions and chemical compounds and processes for their preparation. More particularly, it relates to novel ring-open nucleoside and nucleotide analogues and the like, which show bioregulation activity, and processes for their synthesis.

BACKGROUND OF THE INVENTION AND PRIOR ART

Nucleosides comprise a D-ribose or 2-deoxy-D-ribose sugar unit, chemically bonded to a purine or pyrimidine base selected from adenine, cytosine, guanine, thymine and uracil, via a nuclear nitrogen atom of the base. Since they are units of nucleic acids found naturally in living cells, it has been speculated previously that nucleosides and nucleotides and their related analogs might have potential as chemotherapeutic agents. Any practical value they may have, however, is often greatly reduced by their ready deamination in vivo by deaminases. Studies have been conducted to determine the relationship between structure and activity for both substrates and inhibitors of adenosine deaminase, some such studies involving ring-opened analogues of nucleosides. To date, however, despite several promising reports of novel compounds, no such compounds have been produced and developed for chemotherapeutic use. The present invention provides certain novel biologically active dinucleotide and nucleoside analogues and processes for their preparation. The nucleoside analogues of the present invention have the general formula:

$$RO-CH_2-CH-O-CH_2-B \quad (I)$$
$$\quad\quad\quad\quad\; |$$
$$\quad\quad\quad\quad CH_2-OR'$$

wherein R and R' are independently selected from hydrogen, silyl, substituted silyl, lower alkyl of 1–6 carbon atoms, and phenyl-substituted lower alkyl of 1–6 carbon atoms, and B represents an optionally substituted purine or pyrimidine base selected from the group consisting of adenine, guanine, cytosine, uracil and thymine.

The dinucleotide analogues of the present invention have the general formula:

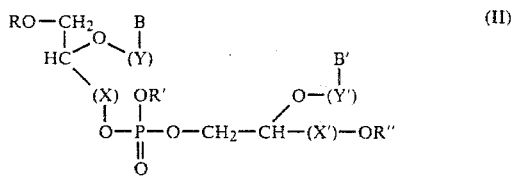

wherein

B and B' represent purine or pyrimidine base compounds independently selected from the group consisting of adenine, cytosine, thymine, guanine and uracil;

each of (X) and (Y) represent methylene groups or (X) and (Y) together represent the group

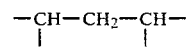

completing a deoxyribose ring;

each of (X') and (Y') represent methylene groups or (X') and (Y') together represent the group

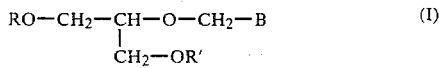

completing a deoxyribose ring;

with the proviso that the compound contains not more than one deoxyribose ring;

and R, R' and R'' are each independently selected from hydrogen, lower alkyl of 1–6 carbon atoms, phenyl substituted alkyl of 1–6 carbon atoms, halogen substituted alkyl of 1–6 carbon atoms, silyl and substituted silyl.

It will be appreciated that the compounds according to the present invention are closely analogous in structure and groupings to naturally occurring nucleosides and nucleotides. The essential chain arrangements and lengths are maintained. The appropriate O and OH functional groups, which in biological environments actively bind to biological centers, are maintained in their natural sequences and disposition relative to the base, but optionally modified with "protecting" groups. Indeed, the groups adjacent to the bases are so similar in chemical constitution to deoxyribose compounds that they can assume the essential conformation of the deoxyribose ring under appropriate conditions. The fundamental difference is that the compounds of the present invention lack the structural rigidity of carbohydrate ring, which renders them unpredictably different in properties and behaviour. Also, the C-4' position is not chiral, in compounds of formula I, so tht stereoisomers do not arise. Each hydroxyl is primary. There can be no syn-anti isomerism about the glycosidic band.

DESCRIPTION OF THE PREFERRED EMBODIMENTS

The preferred bases B in the compounds of the present invention are the purine bases adenine and guanine, with the most preferred being adenine. Compounds of adenine abound in nature, and show wide ranges of biological activity. It is among adenine compounds of the present invention that the most biologically active compounds are found. Test procedures for characterization and evaluation, e.g. with specific enzymes, are well established in connection with adenine compounds.

In contrast with natural adenosine compounds and most of the previously reported synthetic analogues thereof, the adenine compounds of the present invention are resistant to attack by adenosine deaminase enzymes found in most mammalian tissue, and deactivation thereby. Natural and previously reported synthetic analogues of adenosine compounds are attacked by this enzyme in vivo, with the result that the amine group at C6 on the purine ring is hydrolyzed to hydroxyl, forming the corresponding inoxine compound, the majority of which are biologically inactive. With compounds subject to this reaction, the results of tests of biological activity carried out in vitro do not provide any useful guide to in vivo activity.

The compounds of the present invention, however, are very poor substrates for adenosine deaminase, and consequently do not deaminate in vivo, at least to any significant extent. Consequently, test results obtained in vitro are also obtainable in vivo.

Most preferred of compounds of formula I is that in which R and R' are both hydrogen and B is adenine, namely compound of general formula:

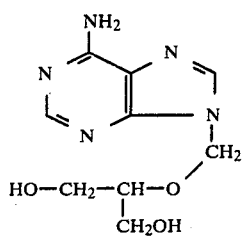

(III)

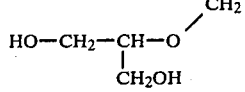

9-[[2-hydroxy-1-(hydroxymethyl)-ethoxy]-methyl]adenine, and the corresponding compounds in which one or both of R and R' represent dimethyl-tert.butylsilyl.

Compounds of general formula I may be made by coupling the appropriately halogenated base with the appropriate alkyl residue. The synthesis may be initiated by treating 1,3-dichloro-2-propyl with sodium benzylate under a nitrogen atmosphere to prepare the chloromethoxy derivative, care being taken to remove excess water. This derivative may be coupled to the appropriately halogenated base, such as 6-chloropurine, in DMF using triethylamine as acid scavenger. Treatment of the chloro compound so formed with methanolic ammonia in a steel reaction bomb gives the 6-amino derivative. The product may be debenzylated to give a compound of formula I, e.g. with hydrogen over palladium oxide in methanol. Protecting groups, if desired, are put on by standard, known methods.

Preferred of compounds of general formula II are those in which B and B' are both adenine; R is hydrogen or monomethoxy trityl; R' is hydrogen or trichloroethyl; R" is hydrogen or tert. butyl dimethyl silyl; and (X), (X'), (Y) and (Y') are as defined above.

Specific, most preferred compounds of this second class according to the invention include the following:

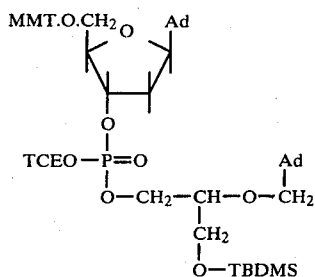

(IV)

where MMT is monomethoxytrityl, AD is adenine, TCE is trichloroethyl and TBDMS is tertiary-butyl-dimethylsilyl;

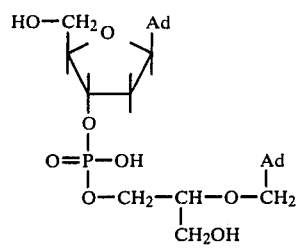

(V)

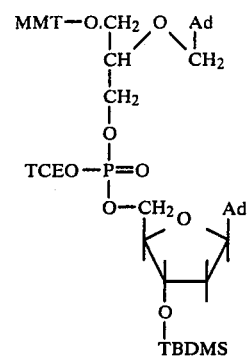

(VI)

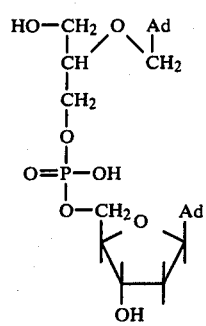

(VII)

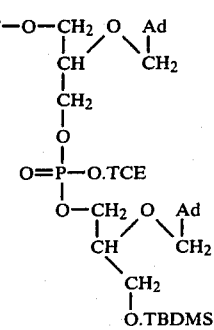

(VIII)

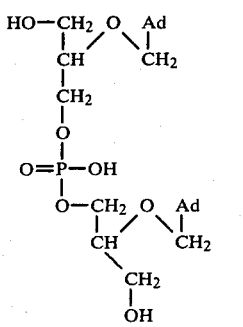

(IX)

The corresponding compounds in which adenine is replaced by the other bases thymine, guanine, cytosine and uracil are also of interest.

The diphosphate compounds of the invention, of general formula (II) may be prepared from suitably protected compounds of formula (I), in which R and R' represent blocking groups such as trityl, substituted trityl, silyl and substituted silyl, which are coupled together by reaction with appropriately protected phosphite or phosphate compounds. Preferred is the so-called dichloridite procedure, in which a first protected compound of formula (I) is reacted with trichloroethyl (or otherwise blocked) phosphodichloridite, in the presence of the 3'-blocked nucleoside or ring-opened nucleoside of formula I to which it is to be coupled. The dichloridite coupling procedure has the advantage that it does not require protection of the amino groups on the base. It is followed by suitable oxidation of phosphite to phosphate. When it is required to obtain unblocked, coupled products, of formula (V), (VIII) or (IX) then deprotection is undertaken by successive treatments. For example, firstly acetic acid may be used to remove MMT; then Zn/Cu in dimethyl-formamide to remove TCE; and finally tetrabutylammonium fluoride in tetrahydrofuran to remove the silyl group.

Several of the compounds of the present invention show anti-viral activity, accompanied by low cell toxicity, rendering them potentially useful in therapeutic compositions to combat specific viral invaders of living mammalian cells. For example, the compound 9-[[2-hydroxy-1-(hydroxymethyl)-ethoxyl-methyl]-adenine, is active against herpes simplex virus, an influenza or cold virus, and against vesicular stomatitis virus, rendering it useful in treatment and/or prevention of rabies. Also, mono-O-tert. butyldimethyl silyl-9-[[2-hydroxy 1-(hydroxy-methyl)-ethoxyl-methyl]-adenine is active against influenza A virus. In both cases, these compounds are active to combat the viruses, and prevent or at least substantially inhibit the replication thereof, at a dosage level at which they are non-toxic to mammalian cells. Others of the compounds of the present invention show a very high degree of toxicity to mammalian cells even at low dosages, rendering them useful as poisons, in the rodenticide field. Bis-O-tert. butyldimethyl silyl-9-[[2-hydroxy-1-(hydroxymethyl) ethoxy]methyl]-adenine is an example of such a toxic compound. Such compounds show in addition utility as insecticides. In general, it may be concluded that compounds of formula I, according to the invention in which R and/or R' represents hydrogen and B represents a purine base, namely adenine or guanine, will show anti-viral activity at appropriately chosen dosage levels without undue toxicity. Compounds of general formula I in which neither R nor R' is hydrogen and in which B represents adenine or guanine on the other hand, are toxic and have potential utility as poisons. It may similarly be concluded that compounds of general formula II behave similarly to the analogous compounds of formula I, on account of the fact that they are in effect phosphate-linked dimers of the formula I compounds, analogous to the dinucleotides of the similar natural compounds.

Certain compounds of the aforementioned formula I in which the purine or pyrimidine base group B is substituted on the nucleus are also of interest as potential pharmacological agents e.g. anti-virals. Specific such compounds are those in which B represents uracil substituted at the 5-position with fluoro or hydroxymethyl; guanine or adenine substituted at the 8-position with halogen (especially but not limited to bromine), thio or amino.

The invention is further illustrated in the following non-limitative examples.

EXAMPLE 1

Preparation of 9-[[2-hydroxy-1-(hydroxymethyl)-ethoxy]-methyl] adenine(III)

6.5 m.moles of 6-chloropurine was condensed with 1,3-dibenzyloxy-2-chloromethoxypropane (6.5 m.moles) in dimethylformamide (4 ml) containing triethylamine (6.5 m.moles) at 25° C. for 16 hours. The product so formed, 1,3-dibenzyloxy-2-(6-chloropurine)-methoxy propane, was isolated from TLC plates as an oil, and subsequently heated in a steel bomb at 90° C. for 20 hours with 60 ml. methanol saturated (0° C.) with ammonia. The solvents were evaporated and 1,3-dibenzyloxy-2-adenine-methoxypropane obtained on precipitation from ethanol with ether. The compound was debenzylated using palladium oxide in methanol at 25 psi of hydrogen for 20 hours. The catalyst was removed by filtration, and on concentrating and cooling the methanol solution, the product 9-[[2-hydroxy-1-(hydroxymethyl)-ethoxy]-methyl]-adenine (III) crystallized as a white solid. The overall yield from 6-chloropurine was 27% melting point—184°–186° C.

m/e (molecular weight 239, $\lambda_{max}^{EtOH}$ 32 259 nm; $R_f$ 0.12 (CHCl$_3$—Et OH, 4:1).

EXAMPLE 2

From compound III prepared according to Example 1, mono-O-tert. butyldimethyl silyl-9-[[2-hydroxy-1-(hydroxymethyl)-ethoxy]methyl]-adenine (compound X) and bis-O-tert.butyldimethyl silyl-9-[[2-hydroxy-1-(hydroxymethyl)ethoxy] methyl-adenine] (compound XI) were prepared by reaction with appropriate controlled amounts of tert. butyl silyldimethyl chloride, in the standard manner for protecting hydroxyl groups according to methods of nucleoside synthesis, followed by standard procedures for separating the two products:

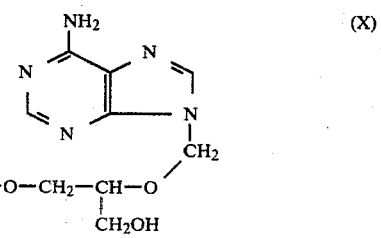

(X)

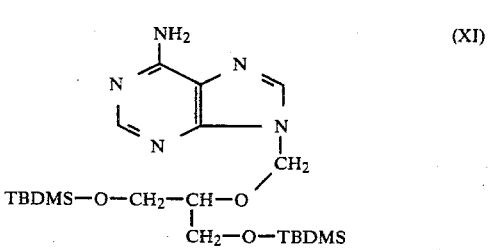

(XI)

where TBDMS represents tert.butyldimethylsilyl.

EXAMPLE 3

Compound III prepared according to Example 1 was tested for activity against viruses. The tests were conducted in the normal way growing mammalian cells in an appropriate medium on a culture disc. In the controls, viral cells were sprinkled onto the growing cell cultures and subsequent growth thereof observed. In the test experiments, both viral cells and compounds according to the invention were sprinkled onto the growing cell cultures.

Then the plaque growth was observed. The reduction in the numbers of the plaques growing in the medium indicates that the added compound is preventing the reproduction of the viral cells. A reduction in the area of the growing plaque indicates a slowing down, inhibition of plaque growth.

Compound III was found to be active to inhibit reproduction of herpes simplex virus. At a dosage of 300 micrograms of compound per ml of medium, the plaque area was reduced by 70%, without showing any evidence of toxicity towards the mammalian cells growing in the culture.

Compound III was also found to be active to prevent reproduction of the VSV (vesicular stomatitis virus), reducing the plaque numbers by 70% at a dosage of 1 mg per ml. Again, no evidence of toxicity to mammalian cells, at this same dosage level, was detected.

EXAMPLE 4

Compound X, prepared according to Example 2, was tested by the procedure described in Example 3 for activity against influenza A virus. It was tested at dosage levels of 0.1, 1.1 and 11 μsg per ml, and at each of these levels was active to inhibit reproduction of the viral cells without demonstrating toxicity towards the mammalian cells. At higher dosage levels (110 μsg per ml) it was toxic to the mammalian cells.

When compound X was similarly tested against the herpes simplex virus, it demonstrated toxicity towards mammalian cells at dosage level of 300 μg/ml, without indicating selective activity against the virus.

Compound XI, in similar tests, indicated a very high level of toxicity towards the mammalian cells, at a dosage level of 30 μsg per ml. when tested against herpes simplex and influenza A viruses.

EXAMPLE 5

Preparation of dinucleotides of general formula II

Appropriately protected compound III was reacted with appropriate nucleosides by standard procedures using the dichloridite procedure (Leitsinger et al, J. Am. Chem. Soc., 98, 365, 1976) which does not require protection of the amine groups on the base. The ratio used was 1 equivalent of tritylated nucleoside, 1.1 equivalents of trichloroethyl phosphorodichloridite and 0.9 equivalents of the 3'-silyl nucleoside, followed by oxidation to phosphate. The protected dinucleotides were deprotected by successive treatments with 80% acetic acid (15 minutes at 80° C.) to remove MMT, Zn/Cu in DMF at 55° C. for 2 hours to remove trichloroethyl, and finally tetrabutylammonium fluoride in THF to remove the silyl groups.

By the above process, the following dinucleotide analogs were prepared.

GENERAL FORMULA II

Compound XII:
   B and B'—thymine;
   R—monomethoxy trityl (MMT)
   R'—trichloroethyl (TCE)
   R''—tert. butyldimethylsilyl (TBDMS)
X and Y complete deoxy-ribose ring
X' and Y'—each $CH_2$
Melting point—110°–112° C.
Compound XIII:
   B and B'—adenine
   Other substituents as compound XII
   Melting point—112°–116° C.
Compound XIV:
   B and B'—thymine
   R, R' and R''—as compound XII
   X and Y—each $CH_2$
   X' and Y' complete deoxy-ribose ring;
   Melting point 87°–88° C.
Compound XV:
   B and B'—adenine
   Other substituents as compound XIV
   Melting point 92°–95° C.
Compound XVI:
   B and B'—thymine;
   X, Y X' and Y'—each $CH_2$
   R, R' and R''—as compound XII
   Melting point 99°–100° C.
Compound XVII:
   B and B'—adenine
   Other substituents as compound XVI;
   Melting point 103°–104° C.
Compound XVIII:
   B and B'—thymine
   R, R' and R''—hydrogen
   X and Y complete a deoxyribose ring
   X' and Y'—each $CH_2$.
Compound XIX:
   B and B'—adenine
   Other substituents as compound XVIII.
Compound XX:
   B and B'—thymine
   R, R' and R''—hydrogen
   X and Y—$CH_2$
   X' and Y' complete a deoxyribose ring.
Compound XXI:
   B and B'—adenine
   Other substituents as compound XX.
Compound XXII:
   B and B'—thymine
   R, R' and R''—hydrogen
   X, Y, X' and Y'—$CH_2$.
Compound XXIII:
   B and B'—adenine
   Other substituents as compound XXII.

Compounds XVIII, XIX and XX were found to be degraded by spleen enzyme. Compound XXII was found to be a good substrate for snake venom enzymes, and for spleen enzyme. Compound XIX was a substrate for spleen enzyme. Compounds XX and XXI are active as biological control regulators.

What I claim is:
1. Compounds of the general formula:

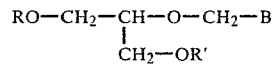

wherein R and R' are independently selected from hydrogen, and lower alkyl-substituted silyl, and B represents an unsubstituted adenine or guanine group linked to the side group shown in formula (I) above at its 9-position.

2. Compounds according to claim 1 in which B represents adenine.

3. Compounds according to claim 2 in which R and R' are independently selected from hydrogen and tertiary butyldimethylsilyl.

4. A compound according to claim 3 wherein both R and R' are hydrogen.

5. A compound according to claim 3 wherein R is tert.butyldimethylsilyl and R' is hydrogen.

6. A compound according to claim 3 wherein both R and R' are tert.butyldimethylsilyl.

REEXAMINATION CERTIFICATE (401st)

United States Patent [19]

Ogilvie

[11] B1 4,347,360

[45] Certificate Issued Oct. 8, 1985

[54] RING OPEN NUCLEOSIDE ANALOGUES

[75] Inventor: Kelvin K. Ogilvie, Candiac, Canada

[73] Assignee: ens BIO LOGICALS Inc., Toronto, Canada

Reexamination Request:
No. 90/000,625, Sep. 12, 1984

Reexamination Certificate for:
Patent No.: 4,347,360
Issued: Aug. 31, 1982
Appl. No.: 187,631
Filed: Sep. 16, 1980

[51] Int. Cl.⁴ .................. C07D 473/18; C07D 473/34
[52] U.S. Cl. ............................... 544/276; 536/23;
536/24; 536/26; 544/277; 544/298; 544/309; 544/313
[58] Field of Search .............. 544/276, 277, 272, 273, 544/265; 424/253; 514/262

[56] References Cited
U.S. PATENT DOCUMENTS
4,323,573  4/1982  Schaeffer .................. 424/253

OTHER PUBLICATIONS
Keller, Biochem Pharm. vol. 30, No. 22, pp. 3071–3077, 1981.

*Primary Examiner*—Nicholas S. Rizzo

[57] ABSTRACT

Nucleoside analogues having a ring-open structure, of general formula

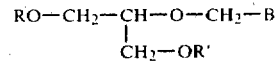

where R and R' may be hydrogen, silyl groups, substituted alkyl groups and the like, and B is a base such as adenine, have been shown to exhibit anti-viral and other biological activities at non-toxic levels. Also provided are phosphate-linked dinucleotide compounds of similar structures.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 5-6 is confirmed.

Claims 1-4 are cancelled.

* * * * *